United States Patent [19]

Pallos

[11] 3,998,621
[45] Dec. 21, 1976

[54] TRIAZINE - ANTIDOTE COMPOSITIONS AND METHODS OF USE FOR COTTON

[75] Inventor: Ferenc M. Pallos, Walnut Creek, Calif.

[73] Assignee: Stauffer Chemical Company, Westport, Conn.

[22] Filed: Jan. 23, 1976

[21] Appl. No.: 651,875

Related U.S. Application Data

[63] Continuation-in-part of Ser. No. 566,654, April 10, 1975, abandoned, which is a continuation-in-part of Ser. No. 450,923, March 13, 1974, abandoned.

[52] U.S. Cl. .................................. 71/93; 71/118
[51] Int. Cl.² ......................................... A01N 9/22
[58] Field of Search .................................. 71/93

[56] References Cited

UNITED STATES PATENTS

| | | | |
|---|---|---|---|
| 2,891,855 | 6/1959 | Gysin et al. | 71/93 |
| 3,131,509 | 5/1964 | Hoffman | 47/57.6 |
| 3,564,768 | 2/1971 | Hoffman | 47/57.6 |

Primary Examiner—Lewis Gotts
Assistant Examiner—Catherine L. Mills
Attorney, Agent, or Firm—Harry A. Pacini

[57] ABSTRACT

Herbicidal compositions comprising an active herbicidal compound of the triazine class selected from 2-chloro-4-ethylamino-6-isopropylamino-s-triazine and 2-(4-chloro-6-ethylamino-s-triazin-2-yl-amino)-2-methylpropionitrile, and antidote therefor, and methods of use; the antidote compound corresponds to the compound 5-norbornene-2,3-dicarboxylic acid mono-(o-methoxy)-anilide having the formula

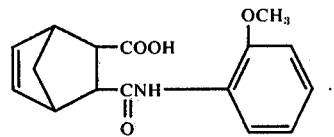

The compound is a new composition of matter.

12 Claims, No Drawings

TRIAZINE—ANTIDOTE COMPOSITIONS AND METHODS OF USE FOR COTTON

This application is a continuation-in-part application of copending application Ser. No. 566,654, filed Apr. 10, 1975, now abandoned which in turn was a continuation-in-part application of then copending application Ser. No. 450,923, filed Mar. 13, 1974, now abandoned.

BACKGROUND OF THE INVENTION

Among the many herbicidal compounds commercially available, the triazines have reached a relatively high degree of commercial success. These herbicides are immediately toxic to a large number of weed pests at different concentrations varying with the resistance of the weed pest. Some examples of the triazine compounds are described and claimed in U.S. Pat. No. 2,891,855.

It has been found in practice that the use of these triazines as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. Nos. 3,131,509 and 3,564,768. These antagonistic agents have not been notably successful. The aforementioned patents specifically exemplify the treatment of seeds employing compounds of a different chemical class not suggestive of the present invention.

DESCRIPTION OF THE INVENTION

It has been discovered that plants of beneficial crop, especially cotton, can be protected against injury by the triazine type herbicides selected from the group consisting of 2-chloro-4-ethylamino-6-isopropylamino-s-triazine and 2-(4-chloro-6-ethylamino-s-triazin-2-yl-amino)-2-methylpropionitrile, alone or mixed with other compounds and/or the tolerance of the plants can be substantially increased to the active herbicidal compound of the above-noted U.S. Patents by adding to the soil, to the seed, or in close proximity to the seed, an antidote compound as a new composition of matter and corresponding to the formula

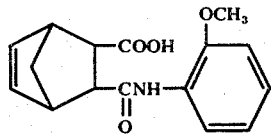

5-norbornene-2,3-dicarboxylic acid mono(o-methoxy)-anilide.

As an alternative mode of action, the compounds of this invention may interfere with the normal herbicidal action of the triazine type herbicides, especially 2-chloro-4-ethylamino-6-isopropylamino-s-triazine and 2-(4-chloro-6-ethylamino-s-triazin-2-yl-amino)-2-methylpropionitrile, to render them selective in their action. Whichever mode of action is present, the corresponding beneficial and desirable effect is the continued herbicidal effect of the triazine with the accompanying decreased herbicidal effect on desired crop species. This advantage and utility will become more apparent hereinafter.

Therefore, the terms herbicide, antidote or antidotal amount, is meant to describe that effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the soil in which a crop is planted. Hitherto, there have been no systems which have been satisfactory for this purpose.

The compound of this invention represented by the above formula can be prepared by several different procedures depending upon the starting materials. The compound of the present invention and the preparation are more particularly illustrated by the following example.

EXAMPLE

Preparation of 5-norbornene-2,3-dicarboxylic acid mono(o-methoxy)-anilide.

5-norbornene-2,3-dicarboxylic anhydride (8.2 g., 0.05 mole) was dissolved in 150 ml. of 1,2-dimethoxyethane. To this solution was added o-anisidine (6.2 g., 0.05 mole). The solution was heated to reflux for one-half hour. After stirring for about 16 hours at room temperature, the solvent reduced to one-half. The solid which separated was separated and dried. There was obtained a yield of 10.4 g. of the title compound. m.p. 151°–154° C.

The compound herein above described was employed in effective herbicidal antidote compositions comprising a triazine herbicide, especially Atrazine (2-chloro-4-ethylamino-6-isopropyl-amino-s-triazine), or Bladex (2(4-chloro-6-ethylamino-s-triazin-2-yl-amino)-2-methyl propionitrile). The compositions may be applied together or separately such that the resultant effect will yield the desired safening effect to the crop or beneficial plant while displaying normal herbicidal effectiveness against the undesired vegetation, i.e. weeds. They were tested in the following manner.

In-Furrow Cotton Antidote Screen

Flats were filled with Felton loamy sand soil. To more closely approximate actual recommended usage on a variety of grass and broadleaf crops in these tests, Atrazine (2-chloro-4-ethylamino-6-isopropylamino-s-triazine) was used in pre-emergence spray application of 1.0 lb/A while constant rate of 5 lb/A of the additives was used. Atrazine 80 W was applied on an individual flat basis by spraying on a linear spray table an amount of stock solution onto the soil application of the additive antidote in-furrow on the planted seed. A stock solution for Atrazine was prepared as follows:

A. 1 lb/A: 1875 mg. of Atrazine 80 W was diluted with 1000 ml. of deionized water and applied with linear spray table so that 1 lb/A was applied per flat.

Additive stock solutions were prepared using 95 mg. of technical material with 15 ml. of acetone 1% Tween 20 so that 1.5 ml. applied to one-half of the flat equals 5 lb/A.

The initial preparatory step was to remove a one pint sample of soil from each flat to be retained and used to cover the seeds after treatment with the additives. The soil was leveled and rows one-quarter inch deep were made lengthwise in each flat. Flats to be treated with 1 lb/A Atrazine 80 W were seeded with Acala cotton (*Gossypium hirsutum*).

After seeding, the flats were sectioned into two equal portions using a wooden barrier and one and one-half ml. of additive stock solution was atomized directly onto the exposed seed and into the furrow in one-half of the flat. The untreated section of the flat served as an herbicide check and also made it possible to observe any lateral movement of the antidote through the soil. The seeds were then covered with the one pint sample of soil removed earlier.

After the treated seeds were covered, the stock solution of Atrazine 80 W was applied on the linear spray table so that 1 lb/A was applied per flat. The flats were placed on greenhouse benches where temperatures were maintained between 70°–90° F. The soil was watered by sprinkling to assure good plant growth.

Injury ratings were taken 2 and 4 weeks after treatments were applied. Individual flats treated with Atrazine 80 W alone at 1 lb/A were included to provide a basis for determining the amount of injury reduction provided by the herbicide antidotes.

After two weeks, the application and presence of the antidote compound exhibited 85% protection to the cotton plants present. After four weeks, 15% protection to the cotton plants was obtained.

PES and PPI Tank Mixes

Flats to be used for growing the crops and weed species were filled with approximately 8 pounds of loamy sand soil approximately 2 inches deep.

The following stock solutions were prepared for use in combination as tank mixes:

A. Herbicides - 2-chloro-4-ethylamino-6-isopropylamino-s-triazine - Atrazine 80 W 380 mg. suspended in 240 ml. of deionized water. Three milliliters of this solution is used to obtain the equivalent application of 1 lb/A (4 mg.) to each flat. 2-(4-chloro-6-ethylamino-s-triazin-2-yl-amino)-2-methylpropionitrile - Bladex 80 W - 48 mg./50 ml. of deionized water. Five milliliters of this solution was used to obtain the equivalent of 1 lb/A per flat.

B. Antidote - of the candidate compound 114 mg. technical material was dissolved in 30 ml. of acetone with 1% Tween 20 (polyoxyethylene sorbitan monolaurate) such that 5 milliliters is equivalent to 5 lbs/A per flat (based on the surface area of a flat).

For the tank mix method of application, 3 ml. of the Atrazine stock solution (A) was combined with 5 ml. of the antidote solution (b) and 5 ml. of Bladex stock solution (A) was combined with 5 ml. of the antidote solution (B). Application was then by the pre-plant incorporation or pre-emergence surface techniques.

For pre-plant incorporation, the mixed or combined stock solution were injected into the soil during incorporation in a 5 gallon rotary mixer. For pre-emergence surface application, the same combination of stock solutions was spray-applied to the soil surface after seeding using an atomizer.

The seeded and treated flats were placed on greenhouse benches where temperatures were maintained between 70°–90° F. The soil was watered by sprinkling to assure good plant growth. Injury ratings were taken four weeks after the applications were made. Individual flats treated with the herbicide alone were included to provide a basis for determining the amount of injury reduction (protection) provided by the herbicide antidotes of this invention.

Acala cotton (*Gossypium hirsutum*) was used as the crop species in this test. Alternating rows of mustard (*Brassica juncea* (L.)), curly dock (*Rumex crispus* (L.)), and foxtail (*Setaria viridis*) were planted in each flat.

When applied as by pre-plant technique, the tank mix (1 lb/A Atrazine and 5 lb/A antidote) completely controlled the weed species, mustard, curly dock and foxtail, whereas the cotton plants (100% injury with Atrazine 1 lb/A) were protected (80% protection). When applied pre-emergence surface, the tank mix (1 lb/A Atrazine and 5 lbs/A antidote) exhibited complete control of the weed species and 85% protection to the cotton plants present in the test flat.

When applied as by pre-plant incorporation technique, the tank mix (1 lb/A Bladex and 5 lbs/A antidote) completely controlled the weed species mustard. Curly dock and foxtail were not included in the test with cotton and Bladex. The cotton plants (70% injury with Bladex 1 lb/A) were protected (86% protection).

The antidote compound and compositions of the present invention can be used in any convenient form. Thus, the antidote compound can be formulated into emulsifiable liquids, emulsifiable concentrates, liquid, wettable powder, powders, granular or any other convenient form. In its preferred form, a non-phytotoxic quantity of an herbicidal antidote compound is admixed with a selected herbicide and incorporated into the soil prior to or after planting the seed. It is to be understood, however, that the herbicides ca be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not affect the herbicidal activity of the herbicides.

The amount of antidote compound present can range between about 0.01 to about 15 parts by weight of antidote compound described herein per each part by weight of herbicide. The exact amount of antidote compound will usually be determined on economic ratios for the most effective amount usable. It is understood that a non-phytotoxic quantity of antidote compound will be employed in the herbicidal compositions described herein.

The herbicides indicated in the tables and elsewhere are used at rates which produce effective control of undesirable vegetation. The rates are within the recommended amounts set forth by the supplier. Therefore, the weed control in each instance is commercially acceptable within the desired or recommended amount.

It is clear that the class of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. With the present invention are prevention of injury to a desired crop species in the presence of a specific compound or combination may be achieved. The beneficial plant species which can be protected by this method is not intended to be limited by the specific crops employed in the example.

The herbicidal compound employed in the utility of this invention is an active herbicide of general type. That is, the members of the classes are herbicidally effective against a wide range of plant species with no discrimination between desirable and undesirable species. The method of controlling vegetation comprises applying an herbicidally effective amount of the herein-described herbicidal compound to the area or plant locus where control is desired. The compositions as set forth in this invention include those wherein the preferred active herbicidal compound is selected from 2-chloro-4-ethylamino-6-isopropylamino-s-triazine, 2-chloro-4,6-bis(ethylamino)-s-triazine, 2(4-chloro-6-ethylamine-s-triazine-2-yl-amino)-2-methylpropionitrile, 2-chloro-4-cyclopropylamino-6-isopropylamino-s-triazine, and combinations thereof.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants", it is meant germinant seeds, emerging seedlings, and established vegetation, including the roots and above-ground portions.

What is claimed is:

1. An herbicide composition comprising a mixture of an effective amount of a triazine herbicide selected from the group consisting of 2-chloro-4-ethylamino-6-isopropylamino-s-triazine and 2-(4-chloro-6-ethylamino-s-triazin-2-yl-amino)-2-methylpropionitrile, and an antiodote compound therefor corresponding to the formula

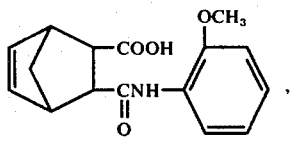

5-norbornene-2,3-dicarboxylic acid mono(o-methyoxy)-anilide; from about 0.01 to about 15 parts by weight of antidote compound for each part by weight of the triazine herbicide.

2. The herbicide composition of claim 1 in which said triazine herbicide is 2-chloro-4-ethylamino-6-isopropylamino-s-triazine.

3. The herbicide composition of claim 1 in which said triazine herbicide is 2-(4-chloro-6-ethylamino-s-triazin-2-yl-amino)-2-methylpropionitrile.

4. In the method of controlling weeds in cotton crops wherein an effective amount of a triazine herbicide selected from the group consisting of 2-chloro-4-ethylamino-6-isopropylamino-s-triazine and 2-(4-chloro-6-ethylamino-s-triazin-2-yl-amino)-2-methylpropionitrile, is applied to the habitat of said weeds, the improvement comprising applying to the habitat thereof to protect the cotton plants from about 0.01 to about 15 parts by weight for each part by weight of the triazine herbicide an antidote compound corresponding to the formula

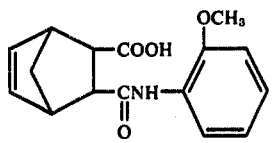

5-norbornene-2,3-dicarboxylic acid mono(o-methoxy)-anilide.

5. In the method of claim 4 in which said triazine herbicide is 2-chloro-4-ethylamino-6-isopropylamino-s-triazine.

6. In the method of claim 4 in which said triazine herbicide is 2-(4-chloro-6-ethylamino-s-triazin-2-yl-amino)-2-methylpropionitrile.

7. The method of protecting cotton crop from injury due to a triazine herbicide selected from the group consisting of 2-chloro-4-ethylamino-6-isopropylamino-s-triazine and 2-(4-chloro-6-ethylamino-s-triazin-2-yl-amino)-2-methylpropionitrile, comprising applying to the triazine treated soil, prior to planting said cotton therein, a non-phytotoxic antidotally effective amount of a compound corresponding to the formula

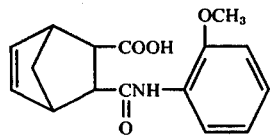

5-norbornene-2,3-dicarboxylic acid mono(o-methoxy)-anilide; from about 0.01 to about 15 parts by weight of said antidote compound for each part by weight of said triazine herbicide.

8. The method of claim 7 in which said triazine herbicide is 2-chloro-4-ethylamino-6-isopropylamino-s-triazine.

9. The method of claim 7 in which said triazine herbicide is 2-(4-chloro-6-ethylamino-s-triazin-2-yl-amino)-2-propionitrile.

10. The method of protecting cotton crop from injury due to a triazine herbicide selected from the group consisting of 2-chloro-4-ethylamino-6-isopropylamino-s-triazine and 2-(4-chloro-6-ethylamino-s-triazin-2-yl-amino)-2-methylpropionitrile, comprising applying to the soil in the rows of the seed prior to treatment of the soil with the triazine herbicide, a non-phytotoxic antidotally effective amount of a compound corresponding to the formula

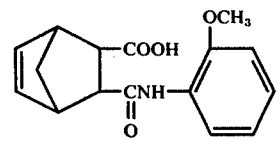

5-norbornene-2,3-dicarboxylic acid mono(o-methoxy)-anilide; from about 0.01 to about 15 parts by weight of said antidote compound for each part by weight of said triazine herbicide.

11. The method of claim 10 in which said triazine herbicide is 2-chloro-4-ethylamino-6-isopropylamino-s-triazine.

12. The method of claim 10 in which said triazine herbicide is 2-(4-chloro-6-ethylamino-s-triazin-2-yl-amino)-2-propionitrile.

* * * * *